United States Patent
Lin et al.

(10) Patent No.: US 6,725,707 B1
(45) Date of Patent: Apr. 27, 2004

(54) IN-SITU LIQUID VISCOSITY MEASUREMENT

(75) Inventors: Yingjie Lin, El Paso, TX (US); Lorenzo Guadalupe Rodriguez, El Paso, TX (US)

(73) Assignee: Delphi Technologies, Inc., Troy, MI (US)

(*) Notice: Subject to any disclaimer, the term of this patent is extended or adjusted under 35 U.S.C. 154(b) by 0 days.

(21) Appl. No.: 10/341,009

(22) Filed: Jan. 13, 2003

(51) Int. Cl.[7] .............................................. G01N 11/00
(52) U.S. Cl. .................... 73/54.01; 73/54.42; 73/53.01
(58) Field of Search ............................. 73/54.01, 61.46, 73/61.76, 54.42, 53.01

(56) References Cited

U.S. PATENT DOCUMENTS

| | | | |
|---|---|---|---|
| 4,277,971 A | 7/1981 | Drzewiecki et al. ............ 73/55 |
| 5,377,531 A | 1/1995 | Gomm ....................... 73/53.05 |
| 5,604,441 A | 2/1997 | Freese, V et al. ............ 324/663 |
| 5,661,233 A * | 8/1997 | Spates et al. ............... 73/61.45 |
| 5,741,961 A | 4/1998 | Martin et al. ................ 73/32 R |
| 5,798,452 A | 8/1998 | Martin et al. ................ 73/32 R |
| 5,942,127 A * | 8/1999 | Wilcox et al. ............... 210/762 |
| 5,947,376 A * | 9/1999 | Moroi et al. ............ 237/12.3 R |
| 6,223,589 B1 | 5/2001 | Dickert et al. ............. 73/61.45 |
| 6,253,601 B1 | 7/2001 | Wang et al. ................ 73/117.3 |
| 6,575,018 B2 | 6/2003 | Berndorfer et al. |

* cited by examiner

Primary Examiner—Hezron Williams
Assistant Examiner—Rodney Frank
(74) Attorney, Agent, or Firm—Jimmy L. Funke

(57) ABSTRACT

A device for determining the viscosity of a liquid has a temperature sensor and a heater disposed in spaced relation within a channel. When the device is immersed in a liquid, the heater heats the liquid and the temperature sensor detects the change in temperature of the liquid in response to heating of the liquid by the heater. A controller coupled with the temperature sensor receives a signal corresponding to the temperature of the liquid and determines an index value corresponding to the change in temperature with respect to time. The index value may be compared with a stored value to evaluate the relative change in viscosity, or it may be used to determine an actual value of viscosity of the liquid.

18 Claims, 4 Drawing Sheets

IN-SITU LIQUID VISCOSITY MEASUREMENT

TECHNICAL FIELD

This invention relates to a viscosity measurement and more particularly, to an in-situ oil viscosity measurement for an internal combustion engine.

BACKGROUND OF THE INVENTION

Internal combustion engine designs have been continually improved to reduce weight, increase fuel economy, increase power output, and at the same time meet environmental emission guidelines. Long term, reliable engine operation requires high quality lubricants, for example, an engine oil, transmission fluid, etc., that are able to meet the strenuous demands of the newer, more efficient engines. In general, an engine oil must be thin enough when first starting the engine to allow for sufficient cranking speed, and the oil must then be able to flow immediately to lubricate vital engine components. Most of the engine wear occurs at start-up before the oil can reach all the engine parts. After the engine has reached its desired operating temperature, the oil must not become too thin as to be unable to provide adequate engine lubrication. After the engine is running, the oil is circulated to the engine components and functions to prevent metal-to-metal contact between the various moving parts.

Thus, the engine oil must be sufficiently thin that it can readily flow to all of the areas of the engine requiring lubrication and sufficiently thick that it is able to form a film of oil over the parts being lubricated to prevent metal-to-metal contact. The viscosity of the oil is a measure of its resistance to flow. The viscosity of the oil should be high enough to maintain the desired oil film, however, if the oil viscosity is too high, it can impede the flow of the oil and also, add excess fluid friction.

The viscosity of engine oil remains relatively constant while exposed to relatively constant environmental conditions, however, an internal combustion engine presents a constantly changing environment in which the engine oil must function. First, the engine experiences a wide range of operating temperatures, and the viscosity of engine oil changes with wide fluctuations of temperature. Further, the viscosity of the engine oil changes as it becomes contaminated. Dirt, oxidation and sludge increase the viscosity of the oil while fuel dilution reduces the viscosity. Oil with too low of a viscosity may breakdown and lose strength at higher engine temperatures. Oils with too high a viscosity may not pump through the engine quick enough to lubricate engine components properly at lower engine temperatures.

To ensure high-performance of modern engines, it is important to change the oil of an engine when the quality of the oil has become degraded. Automobile manufacturers generally provide schedules for changing oil based on estimated service conditions and hours or miles of vehicle use. These schedules are generally not very accurate, due to the wide range of service conditions experienced by individual vehicles. At best, the schedules are very conservative and their inaccuracy may result in engine oil being changed either too soon or too late, with regard to the actual quality of the oil. If changed too soon, the discarded oil is unnecessarily wasted. If changed too late, excessive wear or damage to the engine may result.

One way to monitor the quality of an oil is to measure its viscosity, whereby a change in viscosity provides an indication of when the oil should be changed. In this regard, an increase in viscosity indicates a thickening of the oil, such as may be due to the accumulation of contaminants. Likewise, a decrease in viscosity indicates viscosity breakdown. Prior systems which have been used to measure viscosity have required complicated devices that are best suited to use in a laboratory. Accordingly, obtaining a measurement of viscosity required that a sample of the oil be withdrawn and taken to the lab for measurement with the device. Such systems are thus cumbersome and impractical for determination of viscosity on a regular basis.

Other known devices and techniques that are designed for field measurements are either too expensive or lack the ruggedness to be used in-situ with an internal combustion engine.

Thus, there is a need for an economical, real time, in-situ device and process for measuring engine oil viscosity to detect potentially adverse engine operating conditions.

SUMMARY OF THE INVENTION

The present invention provides a device that may be used to determine the viscosity of a liquid while immersed directly in the liquid. The device has particular utility for use in determining the viscosity of lubricants in an automobile, such as engine oil and transmission fluid, however the device may be used to determine the viscosity of other liquids in other environments as well. The device operates by measuring or sensing the rate of temperature change of the liquid in response to heat added to the liquid (i.e. the speed at which heat travels through the liquid). Specifically, the device takes advantage of the relationship of the viscosity of a liquid with the convective component of heat. Because heating of a liquid generally produces both convective and conductive heating components, accuracy of the viscosity measurement will be improved if the influence of the conductive components of heat can be minimized.

In accordance with the present invention, a device is provided having a heater for heating a liquid and a temperature sensor for detecting a change in temperature of the liquid in response to heating by the heater. The change in temperature with time is used to determine the viscosity of the liquid. In an exemplary embodiment, the device further includes a housing having a channel section and the heater and temperature sensor are disposed within the channel section and are spaced apart a distance which minimizes conductive flow effects from the heater on the temperature sensor. The channel section is sized to optimize the response time of the temperature sensor with respect to sensing temperature change of the liquid due to heating by the heater. In another aspect of the invention, the channel section is sized to minimize turbulent flow of the liquid near the temperature sensor.

In another exemplary embodiment, the device further includes a controller in communication with the temperature sensor whereby the controller may receive a signal from the temperature sensor corresponding to a measured temperature of the liquid. The controller may be integral with the device or it may be a part of a system with which the device is used, such as an automobile. The controller may be configured to calculate an index value corresponding to the change in temperature with time. The index value may either be compared to a previously stored value for evaluation of the relative change in viscosity, or it may be used to determine an instantaneous value of viscosity for the liquid. Thus, in one aspect, the device may be used to detect a relative change in the viscosity of a liquid, to provide an indication when the quality of a liquid has changed to a point that the liquid should be replaced. In another aspect, the device may be used in conjunction with known viscosity values which have been correlated to the rate of temperature change of the liquid to thereby determine an actual viscosity of the liquid.

In yet another aspect of the invention, a method for determining the viscosity of a liquid includes the steps of heating the liquid, sensing the temperature of the liquid at a first time, sensing the temperature of the liquid at a second time, and integrating the change in sensed temperature with time.

The features and objectives of the present invention will become more readily apparent from the following Detailed Description taken in conjunction with the accompanying drawings.

BRIEF DESCRIPTION OF THE DRAWINGS

The present invention will now be described, by way of example, with reference to the accompanying drawings, in which.

DETAILED DESCRIPTION

Figure 1:
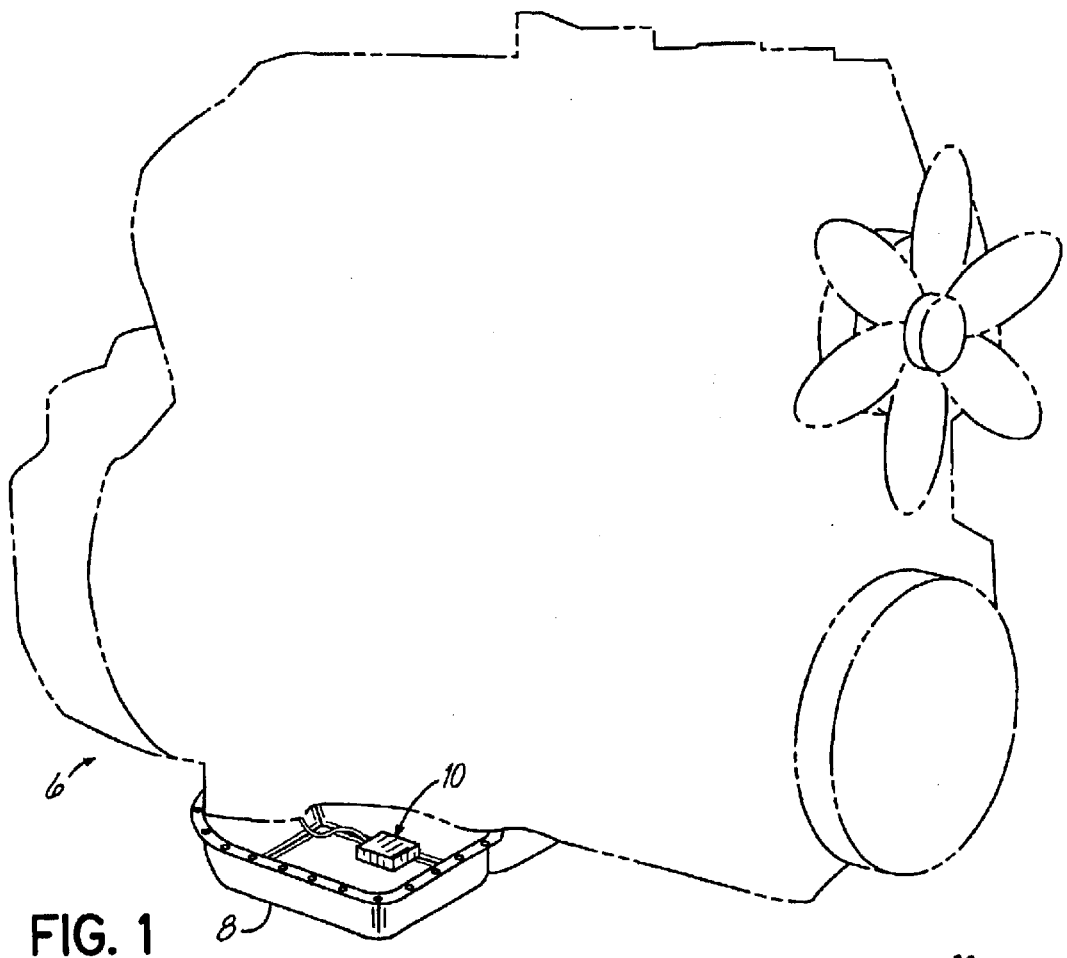
FIG. 1 illustrates an exemplary application of an in-situ viscosity measurement device of the present invention.

The present invention provides a device that can be used to determine the viscosity of a liquid while the device is placed directly in the liquid and without the need for removing a sample of the liquid for testing in a laboratory. Referring to FIG. 1 for example, an internal combustion engine 6 is shown to depict an exemplary application in which a device 10 of the present invention could be used. The device 10 is located in the oil pan 8 where it may be used in-situ to sense the viscosity of oil used to lubricate the engine 6.

Figure 2:
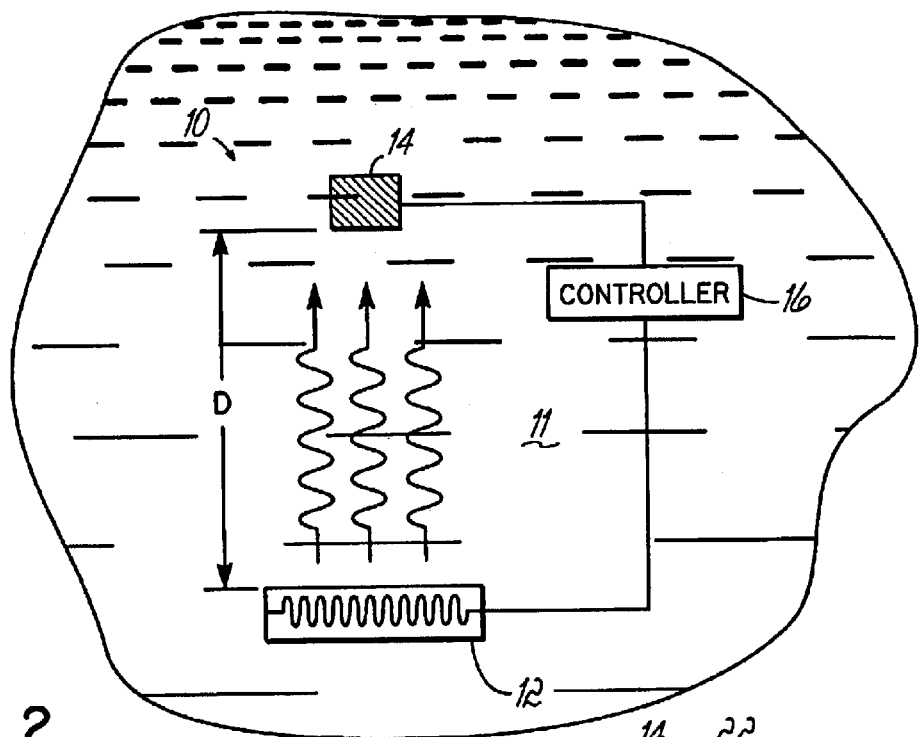
FIG. 2 is a schematic illustration of a device for measuring viscosity in accordance with the principles of the present invention.

With reference to FIG. 2, there is shown a schematic illustration of an exemplary device 10 of the present invention for in-situ determination of the viscosity of a liquid 11, such as oil. The device includes a heater 12 disposed in the liquid 11 and configured to heat the liquid when it is desired to determine viscosity. The device 10 further includes a temperature sensor 14, which is also disposed in the liquid 11 and is configured to detect the change in temperature of the liquid 11 in response to heating of the liquid by the heater 12.

In order to optimize the performance of the device, it is desirable to minimize flow and thermal effects on the temperature sensor 14 which contribute to inaccurate temperature measurements. Optimally, the temperature sensor 14 should be placed in a location where the flow is uniform and laminar. In this context, uniform laminar flow refers not only to the bulk movement of the liquid 11, but also to flow of the liquid 11 due to thermal effects. For example, while the liquid 11 in which the device 10 is placed may be globally static (e.g. not exhibiting bulk movement), it still may exhibit local flow due to the thermal effects caused by the heater 12. Minimizing the flow effects on the temperature measurement can be achieved by locating the sensor 14 an appropriate distance D away from the heater 12 such that turbulent flow effects are minimized. However, it is undesirable to place the temperature sensor 14 a distance D which is too far away from the heater 12 such that the response time of the sensor 14 to the heater 12 is degraded. Accordingly, the temperature sensor 14 should be spaced from the heater 12 a distance D which balances the need to minimize the turbulent flow effects on the temperature sensor 14 while at the same time optimizing the response time of the sensor 14.

Figure 3:
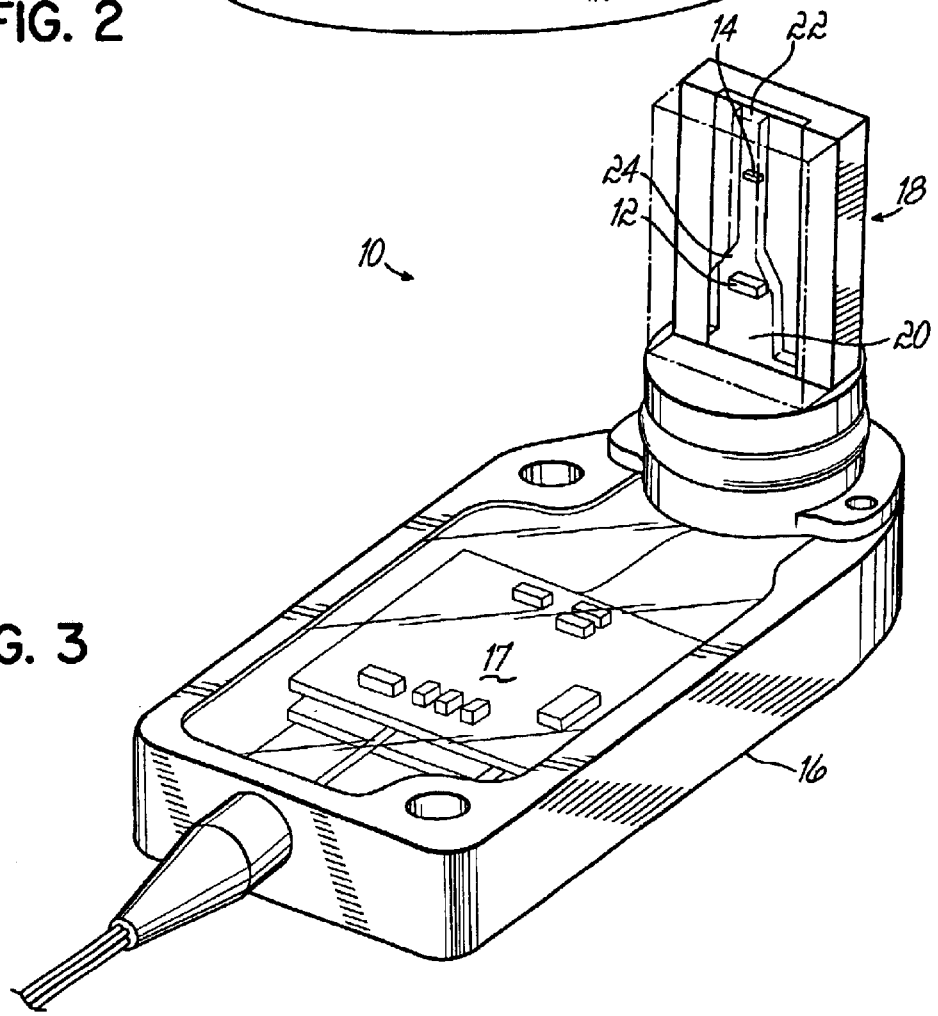
FIG. 3 is a perspective view of one embodiment of the viscosity-measuring device of FIG. 1.

Another aspect of improving the accuracy of the temperature measurement involves minimizing the effects of the environment surrounding the device. For example, heat from a hot engine block may affect the temperature measurement of oil in an oil reservoir adjacent the engine block. Specifically, it is desirable to minimize the turbulent flow effects and the conductive heat effects of the environment on the temperature sensor 14. One way of accomplishing this goal is to place the temperature sensor 14 and heater 12 within a housing 18, as shown in FIG. 3. In the exemplary embodiment shown, the housing 18 is formed at least partially from a material that has a low thermal conductivity, such as Teflon®, or other polymeric material, whereby the temperature sensor is substantially isolated from the conductive heating effects of the environment. An additional benefit of locating the temperature sensor 14 and heater 12 in the housing 18 is that the housing 18 helps to optimize the response time of the sensor 14 to the heater 12 by directing heat from the heater 12 toward the sensor 14

As shown in FIG. 3, the housing 18 includes a channel 20 in which the heater 12 and temperature sensor 14 are disposed. The size of the channel 20 should be selected to permit adequate flow of liquid through the channel 20 while minimizing the turbulent effects of the fluid on the temperature sensor 14 to provide a uniform laminar flow. If the size of the channel 20 is too small with respect to the temperature sensor 14 and heater 12, there will be low flow through the channel 20, and the temperature measurement will be affected. Conversely, if the size of the channel 20 is too big, the flow will be turbulent and will also affect the temperature measurement.

In an exemplary embodiment, the device 10 further includes a controller 16 coupled to the temperature sensor 14 and to the heater 12. The controller 16 may be integral with the device 10, as depicted in FIG. 3, or it may be provided as part of a system with which the device 10 is used, such as the engine control computer of an automobile. The controller 16 includes a driver to energize the heater 12, and a signal conditioner/amplifier for the sensor 14. The controller 16 may further include an integrated circuit 17 having memory for storing data and programmed instructions for performing operations on the data, as may be required.

Figure 4:
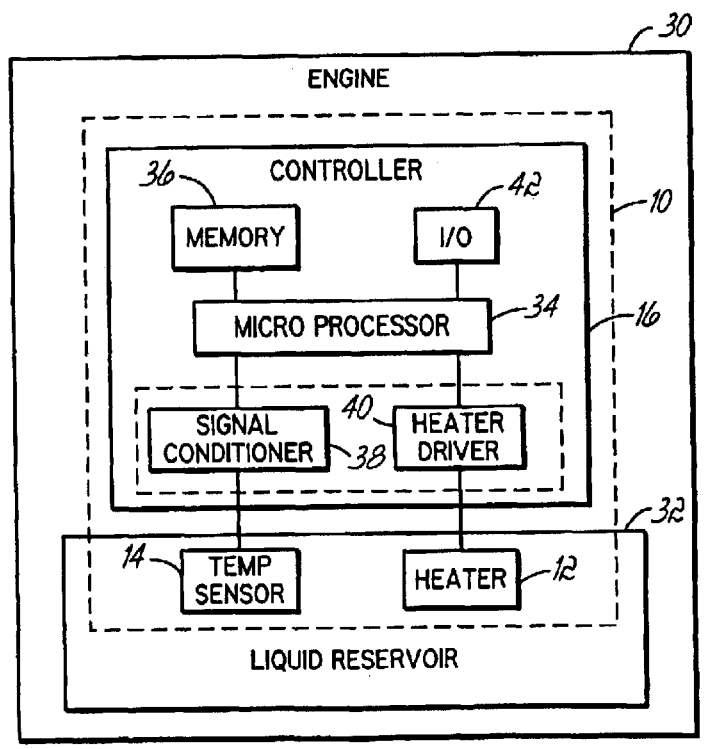
FIG. 4 is a block diagram of an exemplary viscosity-measuring device of the present invention.

FIG. 4 is a block diagram that illustrates an exemplary controller 16 of device 10 used to determine viscosity of oil in an engine 30. The device 10 is disposed in an oil reservoir 32 of the engine 30 whereby the heater 12 and the temperature sensor 14 are immersed in the oil. The controller 16 includes a microprocessor 34 for managing the functions of the controller 16 and for performing calculations on collected data and a memory 36 for storing data and preprogrammed instructions used by the microprocessor 34. A signal conditioner 38 is coupled between the microprocessor 34 and the temperature sensor 14 to amplify signals from the temperature sensor 14. A heater driver 40 is coupled between the microprocessor 34 and the heater 12 to provide power to the heater 12. The controller 16 may include an input/output device 42 adapted to receive input from a user and send signals relating to the operation of the device 10.

The operation of the device 10 to determine the viscosity of a liquid will now be described. As discussed above, the device 10 of the present invention measures the speed of heat in the liquid. More particularly, the device 10 measures the change in temperature of the liquid with respect to time as the liquid is heated. The change in temperature of the liquid with respect to time may be measured while the fluid is moving, such as during the operation of an engine. In such an environment, however, it is difficult to ensure the accuracy of temperature measurements because the temperature and flow characteristics are constantly varying. However, assuming that the environmental effects impose a consistent error on the measured temperature, the device 10 could be used to determine the relative change in viscosity of the fluid over time.

In an exemplary embodiment, the change in temperature of the liquid is measured a period of time after the flow has stopped. In this embodiment, the liquid may be heated for a predetermined duration after the flow has stopped, during which time the change in temperature with time is detected by the temperature sensor 14. The change in temperature with time may then be compared to stored values to determine either a specific value of viscosity for the fluid, or to determine the relative change in viscosity of the fluid with respect to the viscosity measured at a previous time. In the first case, the change in temperature with time may be compared to stored values which have been correlated to actual viscosity or, the change in temperature with time may be used to calculate viscosity using a predetermined formula. For example, the change in temperature with time may be integrated to determine an index value for the fluid. This index value may be compared to a chart of known index values which have been preprogrammed into the controller 16 used in a predetermined formula to determine the associated actual viscosity of the liquid. In the second case, the change in temperature with time may be compared to a value of the change of temperature with time which has been previously calculated and stored, whereby the difference in values may be used to determine when the quality of the liquid has changed by an amount which would necessitate replacing the liquid.

Figure 5:
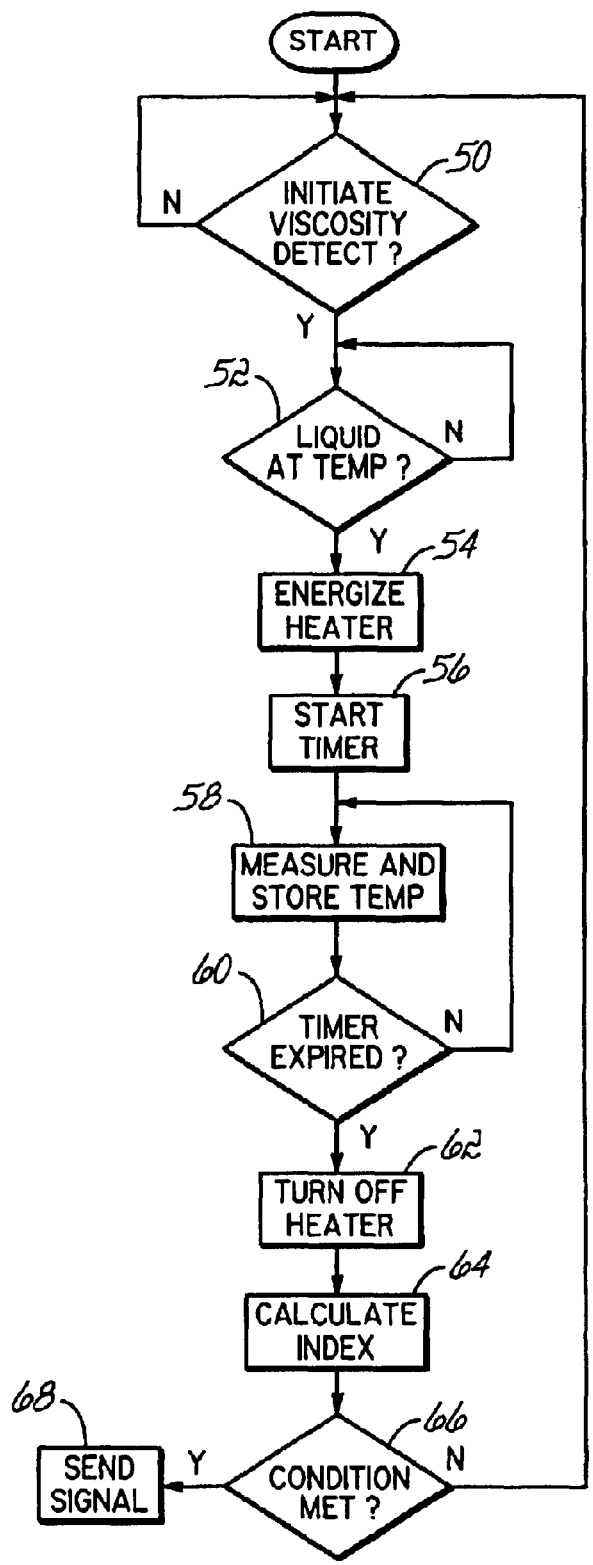
FIG. 5 is a flow chart illustrating an exemplary program for use with a controller of the viscosity-measuring device.

Referring to FIG. 5, there is shown a flowchart illustrating an exemplary cycle of operation of the controller 16, in accordance with the present invention, for determining the viscosity of a liquid with device 10. In step 50, the controller 16 checks to see if a request to initiate a viscosity determination has been received. The request may be initiated automatically, based on an event such as, for example, the starting or stopping of an engine, or the lapse of a predetermined number of miles traveled or hours operated. When a request to initiate determination of viscosity has been received, the controller checks to see if the liquid is at a desired temperature in step 52. When the liquid is at the desired temperature, the controller energizes the heater in step 54 and starts a timer in step 56. The controller then measures and stores the temperature of the liquid at step 58. At step 60, the controller checks to see if the timer has expired. If the timer has not expired, steps 58 and 60 are repeated until the timer has expired, whereby the controller periodically measures and stores temperatures of the liquid during the time duration dictated by the timer. When the timer has expired, the controller turns off the heater in step 62 and calculates an index value in step 64. In step 66, the controller evaluates the index value to see if a condition has been met.

If the condition has been met, the controller sends a signal to the user in step 68. If the condition has not been met, the controller returns to step 50 to await a new request to initiate a viscosity determination.

In one exemplary embodiment, the condition at step 66 may be a comparison of the calculated index value to a stored index value obtained during a previous viscosity determination, whereby the condition is met if the difference between the values exceeds a predetermined amount. Such a condition may be used to determine when the viscosity of the liquid has changed by an amount relative to an earlier determined viscosity.

In another exemplary embodiment, the condition at step 66 may be a comparison of the calculated index value to stored index values corresponding to known viscosities. In this embodiment, the condition is met when a comparison is made and the signal sent at step 68 is an indication of the determined viscosity.

The following example illustrates use of the device 10 to determine viscosity. A device 10 according to the invention, and depicted in FIG. 3, was used to measure the viscosity of various oils. The device 10 included a housing 18 formed from nylon 66, with 33% glass fiber content. A 31-mm long and 3-mm deep channel 20 was formed into the housing 18. At a first end 22 of the channel 20, the width was approximately 3.5 mm, over a length of approximately 18 mm, whereafter the channel 20 gradually widened, over a length of approximately 4 mm at an intermediate portion 24, to a width of approximately 9 mm. A heater 12 comprising a conventional 24-ohm, 1 Watt power resistor was placed in the housing 18, approximately 22 mm from the first end 22 of the channel 20. A temperature sensor 14 (KT 103, SOT-23 package, 2000 ohm silicon temperature sensor available from Infineon Technologies AG, Munich, Germany) was positioned in the channel 20, in the 3.5-mm wide section and at a distance of approximately 14.75 mm from the heater 12. During successive tests, the device 10 was immersed in various oils having known viscosities and the heater 12 was energized to heat each oil to a temperature of 40° C. When the oil being tested reached 40° C., the temperature of the oil was measured using the temperature sensor 14, at periodic intervals for approximately 2 minutes.

Figure 6:
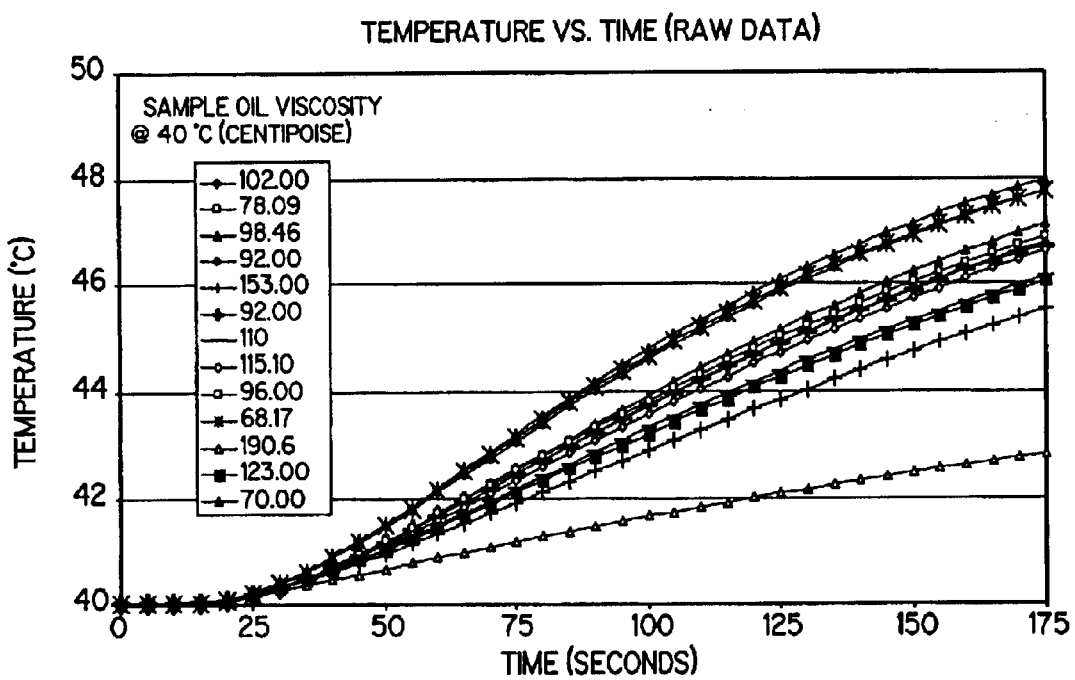
FIG. 6 is a plot of data obtained using the viscosity-measuring device of FIG. 2.

FIG. 6 is a plot of temperature versus time for the data obtained during the tests with the various oils, each having a different viscosity. The area beneath each curve represents the change in temperature with time for the duration of the measurement interval. Accordingly, the area beneath each curve may be determined by integrating the collected data as temperature per unit of time. The areas under the curves can thus be used as sensor index values for correlation to the viscosity of the liquids.

Figure 7:
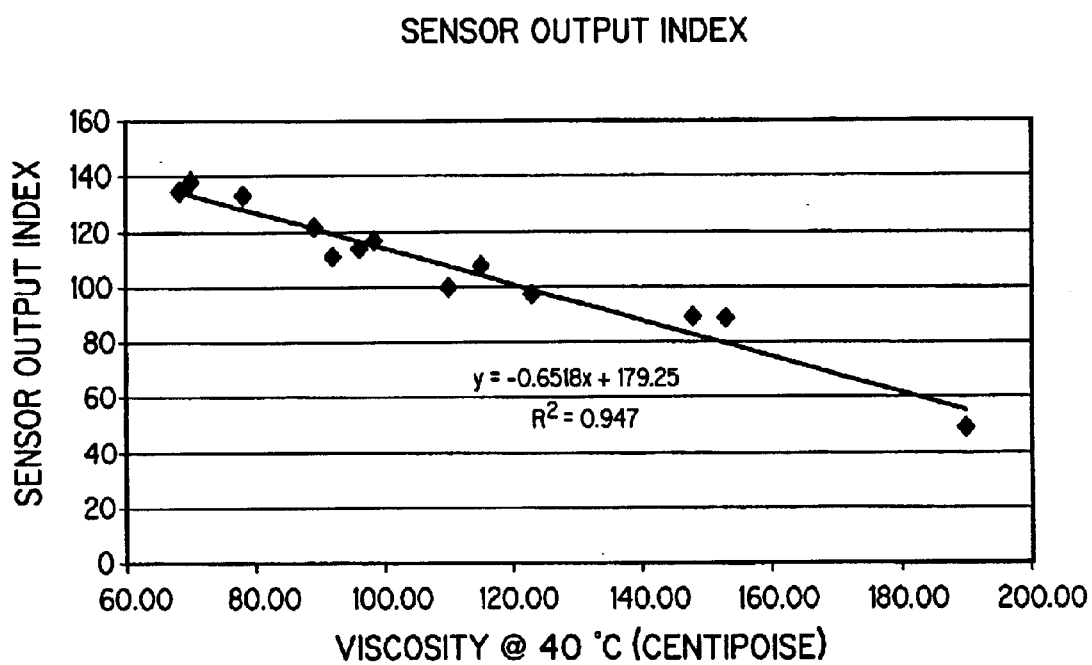
FIG. 7 is a plot of sensor index values from the data of FIG. 6.

In FIG. 7, the sensor index values have been plotted for the data of FIG. 6. A linear curve-fit applied to the plotted data indicates that the sensor index is highly linear, having a coefficient of determination of approximately 0.947. Advantageously, the equation representing the resulting curve-fit line may be utilized to determine the viscosity of a liquid when the device 10 is used to obtain the change in temperature with time, as described above.

While the present invention has been illustrated by the description of various embodiments thereof, and while the embodiments have been described in considerable detail, it is not intended to restrict or in any way limit the scope of the appended claims to such detail. For example, while use of the exemplary device has been described relative to determining the viscosity of liquids such as engine oils, it will be recognized that the device can be used to determine the viscosity of other liquids as well. Additional advantages and modifications will readily appear to those skilled in the art.

The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A device for sensing the viscosity of a liquid, comprising:
   a heater disposed in the liquid and adapted to heat the liquid; and
   a temperature sensor disposed in the liquid and spaced from said heater a distance which minimizes conductive flow effects from said heater on said sensor, said sensor configured to detect a change in temperature of the liquid in response to heating of the liquid by said heater.

2. The device of claim 1, further comprising:
   a housing having a channel section defined by at least one sidewall, said housing disposed in the liquid and said heater and said temperature sensor disposed within said channel section, whereby said heater and said temperature sensor are exposed to said liquid.

3. The device of claim 1, further comprising:
   a controller in communication with said temperature sensor, said controller adapted to receive a signal from said temperature sensor corresponding to a measured temperature of the liquid.

4. The device of claim 3, wherein said controller is configured to store a value representative of a change in temperature of the liquid with respect to time.

5. The device of claim 3, wherein said controller is configured to determine an index value related to the integral of the change in temperature of the liquid with respect to time.

6. The device of claim 3, wherein said controller is further coupled with said heater and is adapted to periodically turn said heater on and off.

7. The device of claim 2, wherein at least a portion of said housing is formed from a material having a low thermal conductivity.

8. The device of claim 2, wherein said channel section is sized to optimize the response time of said temperature sensor with respect to sensing the change in temperature of the liquid in response to energization of said heater.

9. The device of claim 2, wherein said channel section is sized to minimize turbulent flow characteristics of the liquid proximate said temperature sensor.

10. An engine, comprising:
    an oil reservoir for holding engine oil; and
    an in-situ viscosity sensor, including:
       a heater disposed in said oil reservoir, and
       a temperature sensor disposed in said oil reservoir and spaced from said heater a distance which minimizes conductive flow effects from said heater on said sensor, said sensor configured to detect a change in temperature of said oil in response to heating of said oil by said heater.

11. The engine of claim 10, wherein said engine further comprises an engine control computer and said in-situ viscosity sensor is coupled to said engine control computer.

12. The engine of claim 10, wherein said in-situ viscosity sensor further comprises a controller.

13. A method of determining the viscosity of a liquid, comprising:
    heating the liquid in-situ;
    sensing the temperature of the liquid at a first time;
    sensing the temperature of the liquid at a second time; and
    integrating the change in sensed temperature with time.

14. A method of determining the quality of a liquid, comprising:
    heating the liquid;
    sensing the temperature of the liquid at a first time;
    sensing the temperature of the liquid at a second time; and
    comparing the change in temperature with time to a reference value.

15. A method for determining the quality of oil in an engine, comprising:
    heating the oil in the engine after the engine has been stopped;
    periodically sensing the temperature of the oil in the engine;
    calculating a value related to the change in temperature of the oil with time.

16. The method of claim 15, further comprising
    evaluating the calculated value to see if a condition has been satisfied; and
    sending a signal if the condition is satisfied.

17. The method of claim 16, wherein the condition is a predetermined difference between the calculated value and a previously stored value.

18. The method of claim 16, wherein the condition is a correlation to a stored value.

* * * * *